United States Patent [19]

Bryson, III et al.

[11] Patent Number: 4,680,467
[45] Date of Patent: Jul. 14, 1987

[54] ELECTRON SPECTROSCOPY SYSTEM FOR CHEMICAL ANALYSIS OF ELECTRICALLY ISOLATED SPECIMENS

[75] Inventors: Charles E. Bryson, III, Palo Alto, Calif.; Douglas L. Jones, Aloha, Oreg.

[73] Assignee: Kevex Corporation, Foster City, Calif.

[21] Appl. No.: 849,478

[22] Filed: Apr. 8, 1986

[51] Int. Cl.$^4$ .............................................. H01J 49/08
[52] U.S. Cl. .................................. 250/305; 250/309; 250/310
[58] Field of Search ......................... 250/305, 309, 310

[56] References Cited

U.S. PATENT DOCUMENTS 3,665,185  5/1972  Goff ..................................... 250/309
4,587,425  5/1986  Plows .................................. 250/305

Primary Examiner—Craig E. Church
Assistant Examiner—Jack I. Berman
Attorney, Agent, or Firm—Harry E. Aine

[57] ABSTRACT

An electron spectroscopy system is disclosed which is specially suited for chemical analysis of electrically isolated specimens. X-rays or other ionizing radiation is focused to a relatively small spot on the surface of the electrically isolated sample to be analyzed. An electron energy analyzer has its input optics focused such that the input field of view of the electron energy analyzer is coincident with the beam spot produced by the focused beam of ionizing radiation on the specimen so as to capture secondary photoelectrons emitted from the surface of the sample under analysis. The energies of the secondary photoelectrons are analyzed to obtain a spectrum of the constituents of the surface of the sample under analysis. A flood beam of relatively low energy electrons is directed onto the surface of the sample for neutralizing the positive surface charge in the region of the beam spot. An electrically conductive grid is positioned in closely spaced relationship to the surface of the sample for smoothing the gradients in the electrical potential in the region of the beam spot, thereby improving the resolution of the secondary photoelectron energy spectrum obtained from the sample under analysis.

12 Claims, 10 Drawing Figures

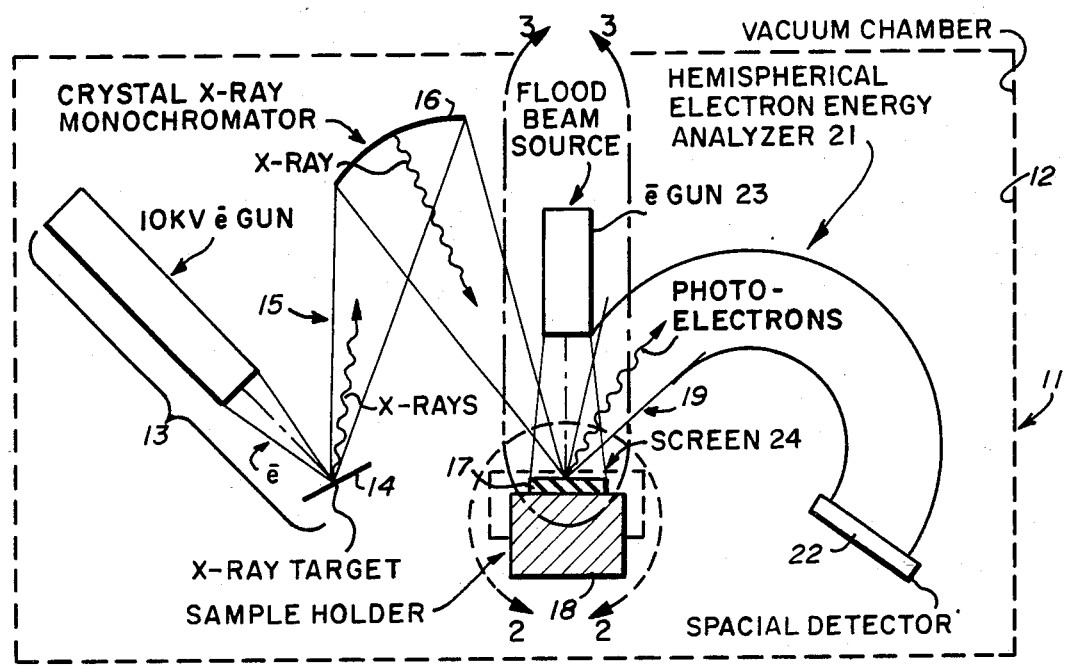
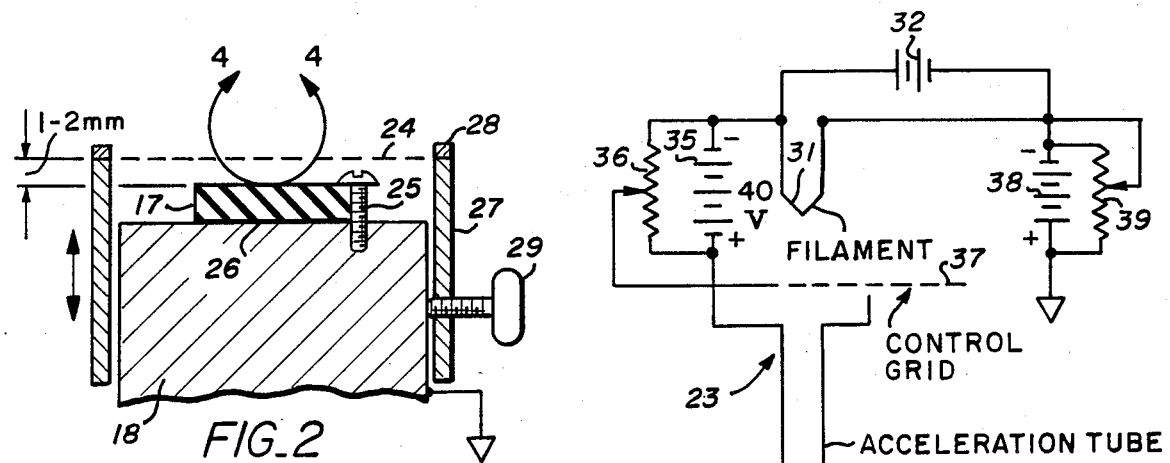
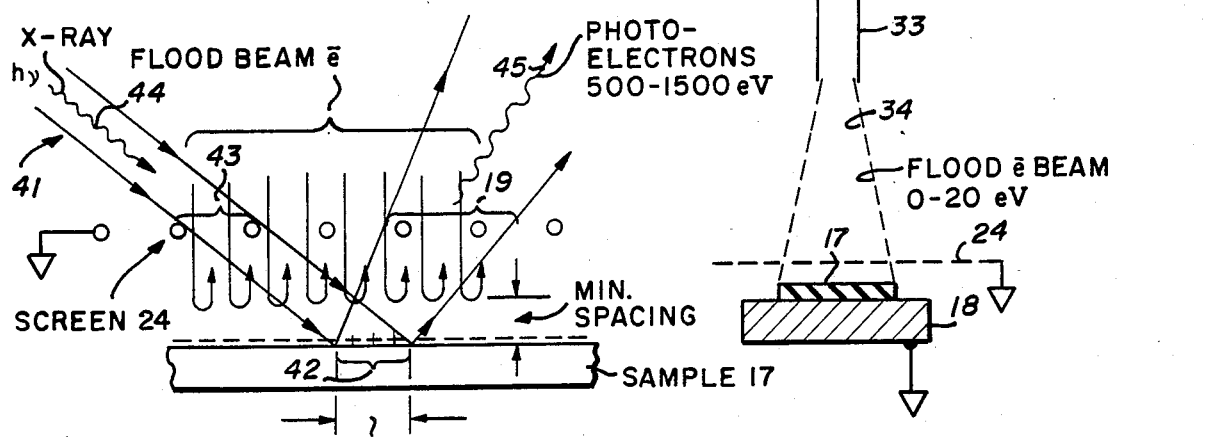

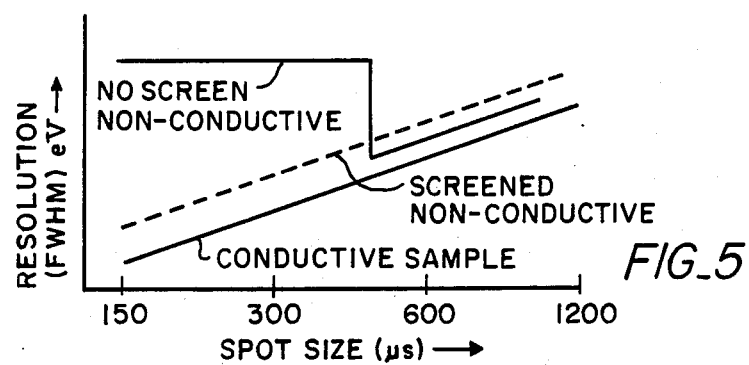
FIG_5
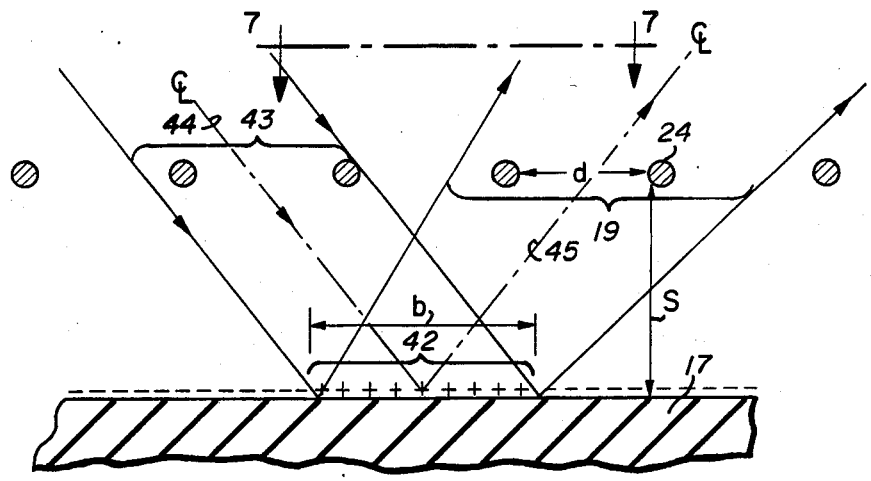
FIG_6
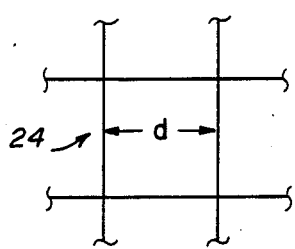
FIG_7a
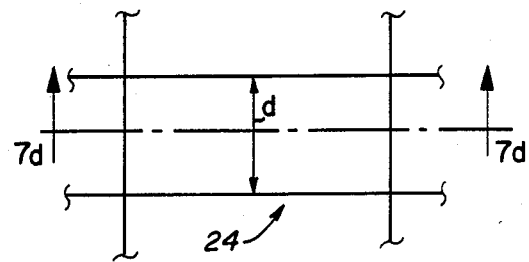
FIG_7b
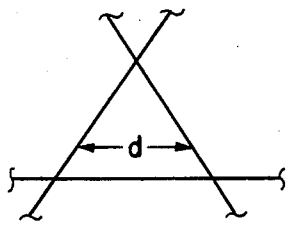
FIG_7c
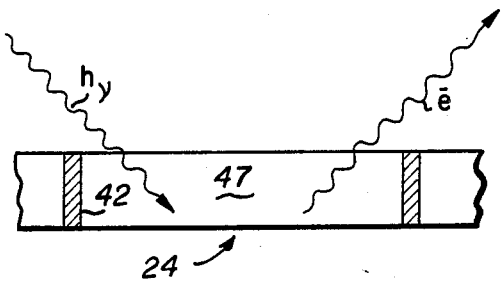
FIG_7d

ELECTRON SPECTROSCOPY SYSTEM FOR CHEMICAL ANALYSIS OF ELECTRICALLY ISOLATED SPECIMENS

BACKGROUND OF THE INVENTION

The present invention relates in general to electron spectroscopy systems for analyzing the surface constituents of electrically isolated specimens. The specimen is bombarded with x-rays of a given energy to produce resultant photoelectron emission which is thence energy analyzed to produce a spectrum of the constituents on the surface of the specimen under analysis. Such systems are commonly referred to as ESCA systems which stands for Electron Spectroscopy for Chemical Analysis.

DESCRIPTION OF THE PRIOR ART

Heretofore, ESCA systems have been employed for analyzing the surface of specimens. In such systems, especially of the small spot size type, a high voltage electron gun bombards an x-ray target to produce a beam of x-rays which are collected by a crystal x-ray monochrometer and focused to a relatively small beam spot on the surface of the specimen to be analyzed. In a typical example, the beam spot diameter on the sample is within the range of 100 to 600 microns. The typical energy of the x-ray beam is 1,486.6 e.V. and produces substantial photoelectron secondary emission from the bombarded beam spot. An electron energy analyzer is disposed such that its entrance field of view is focused on the irradiated beam spot for analyzing the energies of the secondary photoelectrons. In a typical example, the electron energy analyzer is of the hemispherical or spherical type to produce a spatial distribution of the electrons on a spatial detector in accordance with the energy of the photoelectrons entering the analyzer so as to produce an output spectrum of the surface of the sample under analysis.

Examples of such prior art ESCA systems can be found in one or more of the following U.S. Pat. Nos. 3,777,156; 3,617,741; 3,772,522; 3,777,159; and 3,567,926 the disclosures of which are hereby incorporated by reference in their entirety.

In such prior art systems, when analyzing electrically conductive specimens, i.e., the surface under analysis is electrically conductive, the resolution of the electron energy spectrum derived from the sample under analysis generally improves with decreasing spot size. However, when the specimen or the surface of the specimen which is under analysis is electrically isolated or electrically non-conductive, the resolution, with beam spot sizes less than approximately 600 microns in diameter, generally remains at a relatively poor resolution with decreasing spot size. This effect is caused by the secondary photoelectrons leaving behind on the electrically isolated surface a positive surface charge, which for relatively small beam spots, produces a relatively large gradient in the potential at the surface of the sample over the area of the beam spot. As a consequence, secondary photoelectrons leaving this area of positive surface charge have different energies, thereby tending to smear out the linewidths of the energies of the electrons being analyzed by the electron energy analyzer.

Heretofore, in an effort to control this potential gradient at the surface of the insulative material, the sample is flooded with a low energy stream of electrons. These flood electrons tend to neutralize or cancel the positive surface charge at the beam spot. Since it is impossible to exactly cancel the positive surface spatial charge distribution, it is usual practice to use an excess of flood electrons to produce a negative potential on the surface. Once the sample potential reaches the flood electron beam energy, most of the electrons are reflected from the surface and a balance is maintained. This problem arises when the sample is moderately large. If the lateral dimensions of the sample exceed a millimeter or so more than the lateral dimensions of the x-ray beam spot, then, the negative potential of the sample produces fields that force most of the flood electrons to reflect too far from the surface to be effective. As a result, the potential distribution across the beam spot is non-uniform and the energy distribution of the photoelectrons is broadened, an undesirable effect.

In the past, attempts have been made to reduce the potential gradients across the beam spot surface. These attempts have included cutting the sample to a small size, placing a metal mask with a hole one to two millimeters larger than the beam on the sample, reducing the area of the flood electron beam, and using very high flood beam currents. None of these prior attempts have been very successful in improving the resolution of the spectrometer with relatively small beam spot sizes, i.e., less than 600 microns.

It would be desirable to provide a method and apparatus for improving the resolution of the ESCA spectra at small beam spot size, when sampling an electrically isolated or nonelectrically conductive specimen.

SUMMARY OF THE PRESENT INVENTION

The principal object of the present invention is the provision of an improved electron spectroscopy system for analyzing electrically isolated or electrically insulative specimens.

In one feature of the present invention, an x-ray and electron transparent electrode is closely positioned overlaying in spaced relation from, the insulative specimen surface and is operated at a potential so as to allow the flooding electrons to pass through the transparent electrode and to be reflected in the region between the transparent electrode and the specimen. The spacing between the transparent electrode and the specimen surface is chosen so as to smooth out or reduce the amplitude of the potential gradient over the beam spot, whereby the resolution of the photoelectron energy spectrum is improved in use.

In another feature of the present invention, the transparent electrode comprises a grid of electrically conductive members.

In another feature of the present invention, the spacing between the grid and the beam spot on the specimen is less than 20 times the characteristic minimum transverse dimension of the beam spot grid.

In another feature of the present invention, the openings in the grid have a characteristic minimum transverse dimension less than twice the minimum transverse dimension of the beam spot on the specimen.

In another feature of the present invention, the bombarding beam of photons is angled relative to the field of view of the electron energy analyzer such that the field of view of the energy energy analyzer does not include that portion of the transparent electrode which is intercepted by the bombarding beam of photons, whereby the detected photoelectron energy spectrum of the specimen is substantially free of photoelectrons emitted from the transparent electrode.

Other features and advantages of the present invention will become apparent upon a perusal of the following specification taken in connection with the accompanying drawings wherein:

BRIEF DESCRIPTION OF THE DRAWINGS

FIG. 1 is a schematic line diagram, partly in block diagram form, of an electron spectroscopy system incorporating features of the present invention, FIG. 2 is an enlarged sectional view of a portion of the structure of FIG. 1 delineated by line 2—2, FIG. 3 is an enlarged sectional view of a portion of the structure of FIG. 1 delineated by line 3—3, FIG. 4 is an enlarged sectional view of a portion of the structure of FIG. 2 delineated by line 4—4, FIG. 5 is a plot of resolution, in electron volts, vs. spot size, in microns, showing the resolution obtained with the screen on a non-conductive specimen and the resolution obtained with a conductive sample without a screen, FIG. 6 is an enlarged view similar to that of FIG. 4, and FIG. 7 (a-d) is a series of plan view of various grid shapes, such as that obtained by a view of the structure of FIG. 6 taken along line 7—7 in the direction of the arrows.

DESCRIPTION OF THE PREFERRED EMBODIMENTS

Referring now to FIG. 1, there is shown an electron spectroscopy system for chemical analysis (ESCA) 11 incorporating features of the present invention. More particularly, the ESCA system 11 includes an evacuable chamber 12 enclosing therein a number of elements including a source of x-rays 13 formed by a 10 kv electron gun which focuses its output beam of electrons onto an x-ray target 14 to produce a lobe of x-rays 15, as of 1486.6 e.V. in energy which are received by a crystal x-ray monochrometer 16 and thence focuses to a relatively small spot, on the order of 100 to 1200 microns in diameter, on a sample 17 under analysis.

In a typical example, the crystal x-ray monochrometer 16 comprises a diffraction crystal mounted on a Roland circle in the manner disclosed in the aforecited U.S. Pat. Nos. 3,772,522 and 3,777,156 issuing on Nov. 13, 1973 and Dec. 4, 1973, respectively.

The sample 17 is carried upon the upper surface of a sample holder 18 as of aluminum. The incident beam of x-rays generates a lobe of secondary photoelectrons 19 emanating from the irradiated or bombarded beam spot on the surface of the sample 17 under analysis. Other types of bombarding photons or particles may be employed such as high energy ions, for example, cesium ions to produce the secondary photoelectrons or ions. Alternatively, ultra-violet radiation may be used.

A hemispherical electron energy analyzer 21 including input beam optics, not shown, is disposed for capturing a substantial percentage of the lobe of secondary photoelectrons 19 and for analyzing their energies by spatially separating the electrons in accordance with their energies at the output of the energy analyzer 21. A spatial detector 22 is positioned at the output of the energy analyzer 21 for detecting the spatial distribution of the photoelectrons and, thus, producing an energy spectrum of the photoelectrons emitted from the surface of the sample under analysis. The electron energy analyzer 21 has an input field of view focused at the bombarded beam spot on the sample 17 under analysis.

When the sample 17 is made of an electrically insulative material or is electrically insulated or includes electrically isolated regions on its bombarded surface, a region of positive surface charge is developed at the beam spot due to the emission of the secondary photoelectrons and the inability of charge to flow into the electrically isolated regions for neutralizing the positive surface charge. This region of positive surface charge, at the beam spot, distorts the electric field in the region of the beam spot and, thus, subtracts a certain fraction of energy from the emitted secondary photoelectron. Moreover, the gradient in the potential in the region of the beam spot further smears the energies of the secondary photoelectrons and tends to broaden their spectral peaks.

A flood beam source of electrons 23 of relatively low energy, as of 0-20 volts, directs a flood beam of electrons down toward the surface of the bombarded sample 17 for neutralizing the positive surface charge at the beam spot. In addition, a screen grid 24 is positioned overlaying the bombarded surface of the sample 17 in closely spaced relation thereto for smoothing out the gradient in the electrical potential in the region of the beam spot, thereby increasing the resolution of the secondary photoelectron spectrum obtained from the electrically isolated sample 17.

Referring now to FIG. 2, there is shown, in greater detail, the sample holder 18 and resolution improvement screen 24. More particularly, sample holder 18 includes a cylindrical member 18, as of aluminum or stainless steel, connected to ground potential. The sample or specimen 17 under analysis, in the case it is electrically isolated, may comprise, for example, an oxidized silicon wafer, a passivated silicon wafer, a silicon wafer having photoresist deposited thereon, or a sheet of polyimide or other plastic material, The sample 17 is held to the major face of the sample holder 18 via the intermediary of a screw 25, and/or by means of double sided sticky tape 26.

The potential smoothing grid 24 is mounted in overlaying relationship to the surface of the sample 17 which is to be analyzed by means of a support cylinder 27, as of aluminum or stainless steel. A clamping ring 28 clamps the screen 24 at its periphery to the end of the support cylinder 27. The support cylinder 27 is affixed as by a thumb screw 29 to the sample holder cylinder 18 in electrically conductive relation. In addition, the axial height of the screen 24 over the bombarded surface of the sample 17 is adjustable by adjusting the position of the screen 24 and holding it in the proper position by means of the tightened thumb screw 29.

Referring now to FIG. 3, there is shown the flood electron beam source 23. Briefly, the flood electron beam source 23 includes a thermionic emitting filament 31 heated to thermionic emission temperature by means of current flowing from a battery 32 connected in series with the filament 31. An acceleration tube or anode 33 is disposed to receive and collimate the electrons emitted from the filament and is diposed to direct the flood electron beam 34 onto the sample 17 as supported upon the sample holder 18. The acceleration tube 33 is operated at a positive potential relative to the filament by means of a battery 35 having a potential as of +40 volts.

A potentiometer 36 is connected in parallel with the battery 40 and a control grid potential is derived from the potentiometer 36 and applied to a control grid 37 disposed in between the filament 31 and the acceleration tube 33 for controlling the flood beam electron current. In a typical example, the flood beam current is on the order of 100 microamps, and the beam has a diameter of two centimeters.

A second battery 38 and potentiometer 39 is connected so as to derive a variable potential applied to the filament 31 relative to ground for controlling the potential of the electrons of the flood beam 34. The battery 38 is oppositely poled to that of the accelerating potential battery 35 so as to allow the potential of the flood beam to be adjusted between, for example, 0 and +20 electron volts by adjusting the potentiometer 39.

Referring now to FIG. 4, the operation of the flood beam and smoothing grid 24 is shown in greater detail. The x-ray beam 41, emanating from the monochrometer 16, is focused to a beam spot 42 on the surface of the sample or specimen 17. In a typical example, the beam spot 42 has a minimum transverse (lateral) dimension falling with the range of 100 to 1200 microns.

The incident x-ray photon beam 41 produces a secondary photoelectron beam 29 emanating from the beam spot 42. The ejection of the secondary photoelectrons from the beam spot 42 causes the beam spot 42 to have a positive surface charge which cannot be neutralized by a flow of current on the surface of the electrically isolated sample 17. As a result, gradients in the electrical potential near the beam spot 42 are produced which tend to subtract from the energy of the secondary photoelectrons and to smear the resultant spectrum produced at the output of the electron energy analyzer 21.

The flood beam of electrons passes through the smoothing grid 24 and serves to charge the surface of the electrically isolated sample 17 to a net negative potential and to neutralize the positive surface charge in the region of the beam spot 42. However, the potential gradient over the beam spot 42 is not completely eliminated. The screen grid 24, when placed in relatively close proximity to the surface of the sample 17 tends to flatten out or reduce the gradients in the electrical potential in the region of the beam spot 42. Moreover, the flooding electron beam passes through the screen 24 and is reflected from the negative surface charge on the surface of the sample 17.

The conventional electron optics, at the entrance to the electron energy analyzer 21, are dimensioned and arranged so as to have a field of view 19 focused on the beam spot 42. In this manner, a substantial percentage of the secondary photoelectrons emitted from the beam spot 42 are fed into the electron energy analyzer 21 for efficient use. In addition, the focused input is arranged so as not to capture secondary photoelectrons emitted from other regions within the apparatus. More particularly, the smoothing screen 24 is positioned with a certain minimum spacing from the surface of the sample 17 so that the beam spot 43 of the x-ray beam 41 produced on the smoothing grid 24 is not coincident with the field of view 19 of the electron energy analyzer 21 so that secondary photoelectrons emitted from the smoothing screen grid 24 are not analyzed by the energy analyzer 21. In a typical example, the optical axis 44 of the incident x-ray photon beam 41 is angularly displaced relative to the optical axis 45 of the field of view 19 of the electron energy analyzer 21 by a substantial angle, as of 70.79°. This allows the smoothing grid 24 to be placed relatively closely to the surface of the sample 17, for example, on the order of 1 millimeter.

The conventional electron optics at the entrance to the electron energy analyzer 21 includes, for example, a pair of concentric ellipsoid grids having common focii and being axially spaced apart along the beam entrance axis 45.

Referring now to FIGS. 6 and 7, there are a nubmer of preferred criteria related to the size d of the grid openings in the screen 24, size b of the beam spot 42 and the spacing S between the screen grid 24 and the surface of the sample 17. More particularly, the minimum characteristic lateral dimension d of the openings in the screen 24 are preferably on the order of or less than the minimum characteristic lateral dimension b of the beam spot 42. The spacing S between the surface of the sample 17 and the screen grid 24 is preferably greater than the minimum characteristic lateral dimension d of the openings in the screen grid 24. Also, the spacings between the screen grid 24 and the surface of the sample 17 is preferably less than 20 times the characteristic minimum lateral dimension b of the beam spot 42.

Although the screen grid 24 may comprise intersecting wires, as shown in FIGS. 6 and 7, it may also comprise intersecting vanes 47 or an array of parallel elongated vanes 47 with the direction of elongation being in the direction of the bombarding photons so as to reduce the degree of interception of the photons on the grid 24. (See FIGS. 7b and 7d.)

In a typical example, the screen grid 24 is made of a suitable electrically conductive material such as berylium, copper or stainless steel. Beryllium is a particularly suitable material as it is not a common material and the low energy of its secondary photoelectron energy peak is well out of the way of the normal energies of photoelectrons obtained from samples under analysis. In a typical example, the openings of the screen grid 24 have a characteristic minimum lateral dimension d of 0.12 millimeters to 0.25 millimeters and the spacing S between the surface of the sample 17 and the smoothing grid 24 falls within the range of one to two millimeters, and the beam spot 42 has a characteristic minimum lateral dimension b falling within the range 0.1 to 0.5 millimeters. In a typical example for many electrically isolated materials, the electrons of the flood beam have a potential of approximately +2 electron volts when they pass through the grounded screen grid 24.

Referring now to FIG. 5, the advantage to the use of the smoothing grid 24 in connection with analysis of electricallhy insulative or non-conductive samples is shown. More particularly it is seen that when no smoothing grid or screen 24 is utilized with a non-conductive sample 17, the photoelectron resolution as measured by the full width at half the maximum peak height of a given energy line, remains at a relatively poor value with increasing spot size until the spot size exceeds 500 microns and then improves to an intermediate level and thereafter improving with increasing spot size while remaining slightly poorer than the resolution obtained for an electrically conductive sample. On the other hand, when the smoothing screen grid 24, of the present invention, is used, resolution remains only slightly poorer than that obtained for a conductive sample all the way down to spot sizes of less than 150 microns. This is a very substantial improvement and step forward in the art for chemically analyzing constituents of materials on the surface of electrically insulative samples.

As used herein, the term "ionizing radiation" is defined to include photons, ions, or electrons of sufficient energy to ionize the atoms of the surface being bombarded. The term "secondary emission" is defined to include secondary emission of electrons or ions or ions or electrons scattered from the bombarded surface.

In an alternative embodiment, not shown, the screen grid 24 is operable at a potential independent of ground to facilitate control of the flood electron beam and its neutralizing effect on the beam spot 42.

What is claimed is:

1. In a method for analyzing a specimen under analysis, the steps of:
   bombarding an electrically isolated surface region of the specimen under analysis at subatmospheric pressure with a beam of ionizing radiation to produce secondary emission from the bombarded surface region of the specimen and to cause said bombarded surface region of the isolated specimen to have a resultant positive surface charge;
   flooding the bombarded surface of the specimen with a stream of electrons to neutralize the region of positive surface charge;
   positioning a transparent electrode overlaying the surface of the beam bombarded region of the specimen in spaced relation therewith, said electrode being at least partially transparent to the bombarding beam of radiation and to the resultant secondary emission;
   operating the transparent electrode at a potential relative to that of the surface of the specimen and relative to that of the flooding electron stream such that the flooding electrons pass through the transparent electrode on the way toward the specimen and are reflected in the region between the electrode and the specimen back through the transparent electrode; and
   analysing the energies of the secondary emission emanating from the bombarded specimen and passing through the transparent electrode to obtain an indication of the chemical character of the bombarded surface region of the specimen under analysis, whereby the resolution of the secondary emission analysis is increased in use due to the operation of the transparent electrode.

2. The method of claim 1 wherein the transparent electrode is a grid having a plurality of openings therein and including the step of:
   positioning the transparent grid electrode in overlaying relation to the bombarded surface of the specimen under analysis with the spacing between the grid and the bombarded surface being less than twenty times the characteristic minimum lateral dimension of the beam spot on the specimen.

3. The method of claim 2 wherein the grid openings have a characteristic minimum lateral dimension less than five times the characteristic minimum lateral dimension of the beam spot.

4. The method of claim 3 wherein the grid openings have a characteristic minimum lateral dimension in the range of 1.0 millimeters to 0.01 millimeters and the spacing from the grid to the specimen surface is in the range of 5 millimeters to 0.1 millimeters.

5. The method of claim 1 including the step of:
   focusing the bombarding ionizing radiation to a small beam spot on the specimen, said beam spot having a characteristic minimum lateral dimension of less than one millimeter.

6. The method of claim 1 including the step of:
   angling the incident beam of ionizing radiation relative to the field of view of the secondary emission energy analyzer such that the field of view of the energy analyzer does not include that portion of the transparent electrode intercepting the bombarding beam, whereby the detected energy spectrum of the specimen is generally free of secondary emission emitted from the transparent electrode.

7. In an electron spectroscopy system:
   source means for producing a beam of ionizing radiation along a first axis;
   specimen holder means for holding a specimen under analysis in the beam of ionizing radiation for bombarding an electrically isolated surface region of the specimen to produce a resultant beam of secondary emission and a region of the bombarded specimen having positive electrical surface charge;
   electron emitter means, for flooding the bombarded surface of the specimen with electrons to neutralize the positive surface charged region of the specimen;
   energy analyzer means for analyzing the energies of the beam of secondary emission emanating from the bombarded surface region of the specimen under analysis to obtain an indication of the chemical character of the bombarded surface region of the specimen; and
   electron and ionizing radiation permeable electrode means for disposition overlaying the bombarded surface of the specimen in spaced relation therefrom for passage of the ionizing radiation beam, secondary emission beam, and flooding electrons therethrough, and said electrode means being spaced from the specimen such that the flooding electrons are reflected in the region between said electrode means and the specimen back through said electrode means, whereby the resolution of the secondary emission energy analysis is increased in use.

8. The apparatus of claim 7 wherein said electrode means comprises a grid of electrically conductive wires and wherein said grid is positioned relative to the bombarded surface of the specimen under analysis such that the spacing between the grid and the bombarded surface is less than five times the characteristic minimum lateral dimension of the beam spot on the specimen.

9. The apparatus of claim 8 wherein said grid openings have a characteristic minimum lateral dimension less than five times the characteristic minimum lateral dimension of the beam spot.

10. The apparatus of claim 9 wherein the grid openings have a characteristic minimum lateral dimension in the range of 1.0 millimeters to 0.01 millimeters and the spacing from the grid to the specimen surface is in the range of five millimeters to 0.1 millimeters.

11. The apparatus of claim 7 including:
    means for focusing and bombarding ionizing radiation to a small beam spot on the specimen, said beam spot having a characteristic minimum lateral dimension of less than one millimeter.

12. The apparatus of claim 7 wherein said energy analyzer means has a certain field of view of the specimen and including means for angling the incident beam of ionizing radiation relative to the field of view of the energy analyzer such that the field of view of the energy analyzer means does not include that portion of said transparent electrode means intercepting the bombarding ionizing radiation beam, whereby the detected secondary emission energy spectrum of the specimen is generally free of secondary emission emitted from the transparent electrode.

* * * * *